United States Patent [19]

Inouye et al.

[11] 4,029,881

[45] June 14, 1977

[54] ANTIBIOTIC 9-ACYL-3''-THIOMETHOXYMETHYL-SF-837 COMPOSITION AND PROCESS FOR PREPARING THE SAME

[75] Inventors: Shigeharu Inouye, Yokohama; Shoji Omoto, Tokyo; Taro Niida, Yokohama; Bunzo Nomiya, Tokyo, all of Japan

[73] Assignee: Meiji Seika Co., Ltd., Japan

[22] Filed: Mar. 28, 1973

[21] Appl. No.: 345,752

[30] Foreign Application Priority Data

Apr. 6, 1972 Japan .............................. 47-33897

[52] U.S. Cl. .................................. 536/9; 424/180; 536/17
[51] Int. Cl.² ........................................ C07H 17/08
[58] Field of Search .............. 260/210 AB; 536/17, 536/9

[56] References Cited

UNITED STATES PATENTS

| | | | |
|---|---|---|---|
| 3,792,035 | 2/1974 | Fukatsu et al. | 260/210 AB |
| 3,853,842 | 12/1974 | Kishi et al. | 260/210 AB |
| 3,855,202 | 12/1974 | Omoto et al. | 260/210 AB |

Primary Examiner—Johnnie R. Brown
Attorney, Agent, or Firm—McGlew and Tuttle

[57] ABSTRACT

A new derivative of the macrolide antibiotic SF-837 substance is manufactured by treating a 9,2'-diacyl- or 9-acyl-SF-837 composition with dimethylsulfoxide and acetic anhydride, and, subsequently, with an alcohol or water-containing solvent to yield the novel compound, 9-Acyl-3''-thiomethoxymethyl-SF-837 composition. In addition to high therapeutic effectiveness and low acute toxicity, this novel compound of the present invention has the great advantages that it does not have the bitter taste originally accompanying the parent compounds, and the further advantage that it is suitable for pediatric and veterinary use.

9 Claims, No Drawings

ANTIBIOTIC 9-ACYL-3''-THIOMETHOXYMETHYL-SF-837 COMPOSITION AND PROCESS FOR PREPARING THE SAME

BACKGROUND AND SUMMARY OF THE INVENTION

The present invention relates to a new derivative of a new macrolide antibiotic, SF-837 composition (Japanese Patent Pub. No. 28834/71) which was previously discovered by the present inventors, and the invention also relates to a process for preparing the same. More particularly, the invention relates to a process for manufacturing the 9-acyl-3''-thiomethoxymethyl-SF-837 composition having the formula,

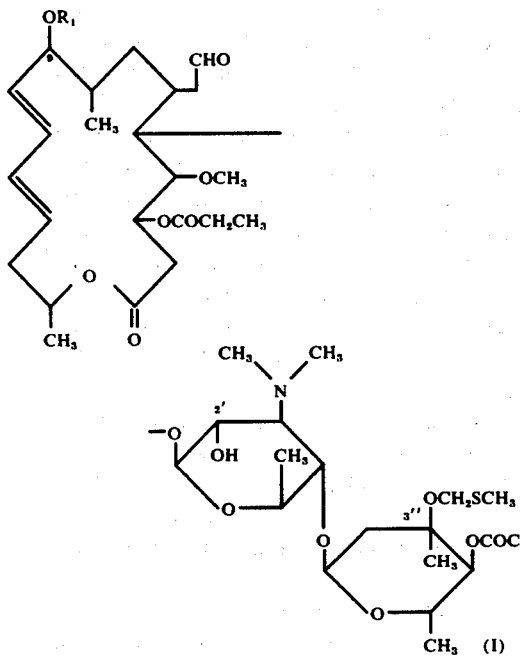

wherein $R_1$ represents an acetyl or propionyl group, wherein a 9,2'-diacyl derivative or a 9-acyl derivative of the SF-837 composition represented by the general formula,

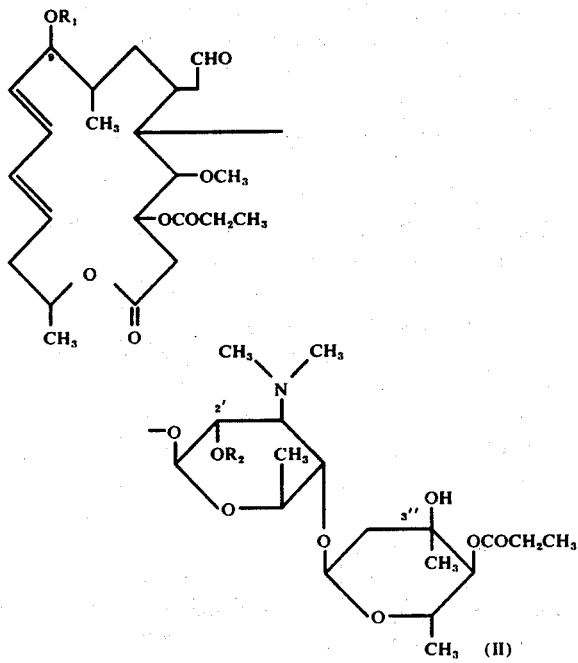

wherein $R_1$ is defined as above and $R_2$ represents a hydrogen atom or an acetyl or propionyl group, is treated with dimethylsulfoxide and acetic anhydride to synthesize the 9,2'-diacyl-3''-thiomethoxymethyl-SF-837 composition represented by the formula,

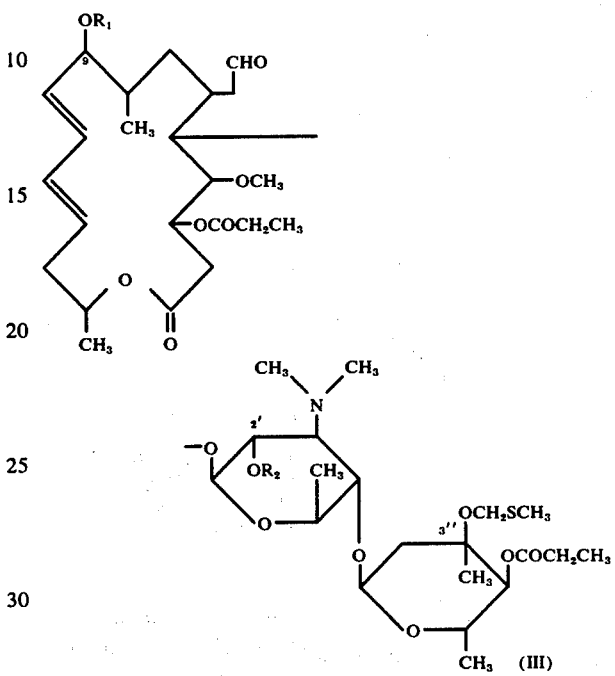

wherein $R_1$ and $R_2$ each represents an acetyl or propionyl group, followed by alcoholysis or hydrolysis of this substance (III).

The base and known acid addition salts of the SF-837 composition, one of the macrolide antibiotics, have a peculiarly objectionable bitter taste, and the oral preparations of these substances have been used in the form of capsules or coated tablets. However, the application of these preparations in the pediatric field has been greatly avoided since they are difficult for infants and children to swallow and their manufacture is uneconomical. In such case, drugs are generally prepared and used as fruit juice suspensions or chewable tablets to exclude these defects, but the intolerable bitter taste of the SF-837 composition still makes it impossible to use this SF-837 composition in the pediatric field. Although the compound of the present invention, i.e., the 9-acyl-3''-thiomethoxymethyl-SF-837 substance, is not completely free from bitter taste, its bitterness is of such a degree as to be acceptable to infants and children. Accordingly, the compound of the present invention is very useful for making preparations for oral administration, such as powders, syrups, and troches, of low toxicity and high therapeutic effectiveness.

Furthermore, the compound of the present invention is of great use in the veterinary field as a drug for swine, which habitually refuse substances having a bitter taste.

The SF-837 substance contains three hydroxyl groups in its molecular structure, as shown in the following formula (Journal of Antibiotics, 24 460–475 (1971)).

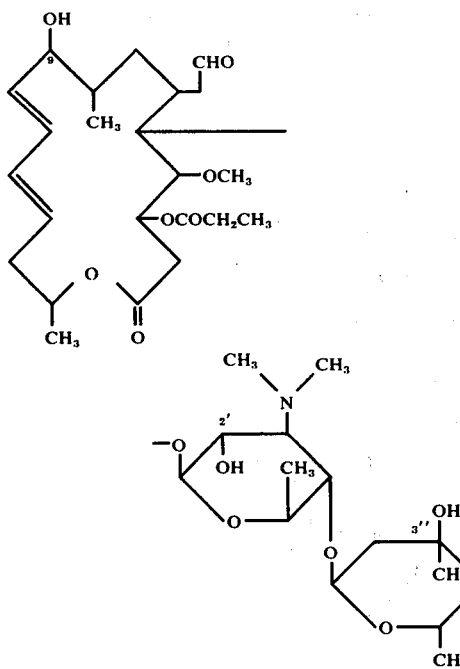

Further, among these three groups, those at the position C-9 and C-2' are relatively high in reactivity and various kinds of derivatives have been synthesized through them (for example, see Japanese Patent Application No. 46796/1971).

On the other side, the tertiary hydroxyl group at position C-3'' is the most inactive among all of said hydroxyl groups and no derivative from this group has been demonstrated.

The present inventors have studied in various ways means for obtaining the derivatives by reaction with the hydroxyl group at this C-3'' position. They have found that, when the present substance is treated with dimethylsulfoxide and acetic anhydride, thiomethoxymethyl group can be introduced into the site of this tertiary hydroxyl group. The present invention in this manner was thus realized.

Prior to this substitutional reaction in the present invention, it was observed that the hydroxyl group at the position C-9 should be protected by acetylation or propionylation otherwise it would be oxidized to a carbonyl group under these reaction conditions that at the position C-2' the hydroxyl group may not be protected because it can be easily acetylated by the action of the acetic anhydride added in the reaction system. Therefore, it has been found that both 9,2'-diacyl-SF-837 substance and 9-acyl-SF-837 substance are available as the starting materials of the present invention, though the former, i.e, the 9,2'-diacyl-SF-837 substance gives a higher yield.

The 9,2'-diacyl-SF-837 substance can be obtained by treating the SF-837 substance with pyridine-acetic anhydride (Journal of Antibiotics, 24 457 (1971)) or with acetylchloride-triethylamine (Japanese Patent Application No. 48096/71). The 9,2'-dipropionyl-SF-837 substance can be obtained by treating the SF-837 substance with pyridinepropionic anhydride (Journal of Antibiotics, 24 473 (1971)) or with propionyl chloride-triethylamine (Japanese Patent Application No. 48096/71). Further, the 9-acetyl-SF-837 substance, or the 9-propionyl-SF-837 substance, can be obtained by treating the SF-837 substance with acetyl chloride, or propionyl chloride, and pyridine (Japanese Patent Application No. 46796/71).

DESCRIPTION OF SPECIFIC EMBODIMENTS

Dimethylsulfoxide and acetic anhydride are used in the present invention as the reaction reagents for obtaining the compounds represented by general formula (III) from the compounds represented by general formula (II). The dimethylsulfoxide also functions as the solvent for dissolving the reaction materials, but, additionally, other solvents inactive to the reaction materials, such as benzene and toluene, are also used as the solvent. The reaction may be conducted at a temperature range of between room temperature and 50° C. However, it is preferable to conduct the reaction at room temperature for 3–5 days. It is noted that the presence of a catalytic amount of pyridine considerably accelerates the reaction and complete the latter within a day. Further, although there remain a trace of pyridine which usually adheres to the 9,2'-diacyl-SF-837 in the course of its preparation, addition of a small amount of pyridine is preferable for shorteniing the reaction time.

After completion of the reaction, excess amounts of the reagents and the solvents are removed by evaporation to obtain the 9,2'-diacyl-3''-thiomethoxymethyl-SF-837 substance. For this purpose, the reaction mixture can, for example, be mixed well with a large amount of benzene or toluene, washed with water and aqueous sodium carbonate solution, and the benzene or toluene layer evaporated to dryness. The 9,2'-diacyl-3''-thiomethoxymethyl-SF-837 substance thus obtained is, if required, further purified by a common procedure using counter-current techniques or chromatography.

When the 9,2'-diacyl-3''-thiomethoxymethyl-SF-837 substance is dissolved in an alcohol, such as methanol or ethanol, or a water-containing solvent, such as aqueous methanol, aqueous ethanol or aqueous acetone, and left to stand, only the acyl group at the position C-2' is selectively detached, resulting in the formation of the desired compound according to the present invention, the 9-acyl-3''-thiomethoxymethyl-SF-837 substance. This reaction can be completed if the resulting solution is kept at room temperature overnight in case of the 2'-acetyl derivative, or at 40° C in case of the 2'-propionyl derivative.

The antimicrobial spectrum of the 9-acyl-3'-thiomethoxymethyl-SF-837 substance obtained according to the present invention is shown in Table 1.

TABLE 1

The antimicrobial spectrum of the 9-acetyl- and 9-propionyl-3″-thiomethoxymethyl-SF-837 substance made according to the invention.

| Microorganisms | | Minimal Inhibitory Concentration (mcg/ml) | | |
|---|---|---|---|---|
| | | 9-acetyl-3″-thio-methoxy-methyl-SF-837 | 9-propio-nyl-3″-thio-methoxy-methyl-SF-837 | SF-837 |
| Escherichia coli | | 50 | 50 | 100 |
| Mycobacterium 607 | | 6.25 | 6.25 | 25 |
| Staphylococcus aureus | | 0.78 | 0.78 | 0.78 |
| Neisseria gonorrhoeae Megurita | | 100 | 100 | 25 |
| Neisseria meningitidis | | 6.25 | 6.25 | 6.25 |
| Mycoplasma gallisepticum | S-6 | < 0.1 | < 0.1 | 0.1 |
| ″ | S-15P | < 0.1 | < 0.1 | 0.05 |
| ″ | S-35P | < 0.1 | < 0.1 | 0.05 |
| ″ | T-4AT (tyrosine-resistant) | 12.5 | 12.5 | > 100 |
| ″ | CH3T | < 0.1 | < 0.1 | < 0.05 |
| ″ | KP-3 | < 0.1 | < 0.1 | < 0.05 |
| ″ | KP-13 | < 0.1 | < 0.1 | < 0.05 |
| Vibrio coli | 34E | 25 | 25 | 12.5 |
| ″ | SD-358 | > 50 | > 50 | > 50 |
| ″ | SD-362 | 25 | 25 | > 50 |

Since the 9-acyl-3″-thiomethoxymethyl-SF-837 substance is inhibitory against Gram-positive bacteria as the SF-837 substance is, it is as well available as an antimicrobial agent. Particularly, it is notable that the in vitro antimicrobial activity of the 9-acyl-3″-thiomethoxymethyl-SF-837 substance of the present invention against *Escherichia coli*, *Mycobacterium*, *Mycoplasma*, and macrolide-resistant Mycoplasma is higher than that of the SF-837 substance. Furthermore, the results of the therapeutic tests using the mice infected by *Staphylococcus aureus* Strain 209P was better with the said 9-acyl-3″-thiomethoxymethyl-SF-837 substance than with its parent substance (see Table 2).

Table 2

Therapeutic effect of the 9-acyl-3″thiomethoxy-methyl-SF-837 substance made according to the invention on the staphylococcal infection of mice in laboratory*).

| Substances | Survival rate in a week after oral administration of 350mg/Kg |
|---|---|
| 9-acetyl-3″-thiomethoxymethyl-SF-837 substance | 90% |
| 9-propionyl-3″-thiomethoxymethyl-SF-837 substance | 90% |
| SF-837 | 37.5% |

*)Infection of mouse intraperitoneally by *Staphylococcus aureus* Strain 209-P.

Another experiment on the therapeutic effect of the present invention demonstrated that, when orally administered to the mice which had been infected fatally by *Staphylococcus aureus* 209-P or *Streptococcus pyogenes* Ti-125 Gr-A Type I, said compound was as effective as the 9-acyl-SF-837 and the SF-837 substances, as shown in Table 3.

TABLE 3

Therapeutic effect of the 9-acyl-3″-thiomethoxymethyl-SF-837 substance against bacterial infections.

A. Treatment of animals infected by Staphylococcus.
Animals tested: ICR-JCL mouse, 4-week old, male, 10 heads for each group.
Bacterium inoculated: Staphylococcus aureus 209-P.
Inoculum size: $15 \times 10^7$ cells/0.5ml/mouse (10 $LD_{50}$).
Method of administration: Samples were suspended in a sterilized 2% aqueous gum arabic solution and administered once to the mice inoculated with the bacterium.

| Substances | Survival rate(%) in each dosage(mg/Kg) | | | |
|---|---|---|---|---|
| | 400 | 350 | 200 | 150 |
| 9-Acetyl-3″-thiomethoxy-methyl-SF-837 | 100 | 90 | 80 | 30 |
| 9-Propionyl-3″-thiomethoxymethyl-SF-837 | 100 | 90 | 70 | 30 |
| 9-Acetyl-SF-837 | 100 | 100 | 100 | 80 |
| SF-837 | 90 | 60 | 40 | 20 |
| Control | 0 | | | |

B. Treatment of animals infected by Streptococcus
Animals tested: The same as in A.
Method of administration: The same as in A.
Bacterium inoculated: Streptococcus pyogenes Ti-125 Gr-A Type I.
Inoculum size: $1 \times 10^7$ cells/0.5ml/mouse($5LD_{50}$).

| Substances | Survival rate(%) in each dosage(mg/Kg) | | | |
|---|---|---|---|---|
| | 400 | 300 | 200 | 100 |
| 9-Acetyl-3″-thiomethoxy-methyl-SF-837 | 100 | 100 | 100 | 100 |
| 9-Propionyl-3″-thio-methoxymethyl-SF-837 | 100 | 100 | 100 | 100 |
| 9-Acetyl-SF-837 | 100 | 100 | 100 | 100 |
| SF-837 | 100 | 100 | 90 | 70 |
| Control | 0 | | | |

Contrary to its high activity against the bacterial infections, the acute toxicity of the compounds of the present invention is very low. Table 4 shows that the toxicity of the 9-acyl-3''-thiomethoxymethyl-SF-837 substance is much lower than those of the SF-837 and 9acetyl-SF-837 substances.

TABLE 4

The acute toxicity of the 9-acyl-3''-thiomethoxymethyl-SF-837 substance

Animals tested: ICR-JCL mice, male.
Samples: Each substance was suspended in a 5% aqueous arabic gum solution.
Method of administration: Intraperitoneal injection.

| Substances | Mortality in each dosage | |
|---|---|---|
|  | 4,000 mg/Kg | 2,000 mg/Kg |
| 9-Acetyl-3''-thiomethoxy-methyl-SF-837 | 0/3 | 0/3 |
| 9-Propionyl-3''-thio-methoxymethyl-SF-837 | 0/3 | 0/3 |
| 9-Acetyl-SF-837 | 1/3 | 0/3 |
| SF-837 | 2/3 | 2/3 |

A panel test has proved that the objectionable bitter taste of the parent material, the SF-837 substance, is reduced by substitution of the hydroxyl groups at the positions C-9 and C-3'' and that the said taste of the compounds of the present invention is almost undetectable (see Table 5).

TABLE 5

Panel tests on the bitter taste.

| Test Compounds*) | Mean Scores**) |
|---|---|
| 9-Acetyl-3''-thiomethoxymethyl-SF-837 | 0.2 |
| 9-Propionyl-3''-thiomethoxymethyl-SF-837 | 0.2 |
| 9-Acetyl-SF-837 | 2.8 |
| SF-837 | 3.6 |
| Erythromycin | 1.8 |
| Leucomycin | 1.9 |

| Scoring standards: | Undetectable | 0 point |
|---|---|---|
|  | Negligible | 1 point |
|  | Bitter (acceptable) | 2 point |
|  | Bitter (unacceptable) | 3 point |
|  | Bitter (objectionable) | 4 point |

Amounts of the dry syrups tested: 100–200 mg each

*)10% by weight dry syrup of each compound in sucrose.
**)Panel size: 10 persons.

From the above data, it is apparent that the compounds of the present invention have an excellent property as an antimicrobial agent for medical preparations.

Details of the present invention will further be explained by the following examples. However, these examples will never limit the spirit and scope of the present invention.

EXAMPLE 1

One gram of 9,2'-diacetyl-SF-837 substance was dissolved in a mixture of 30ml of dimethylsulfoxide and 3ml of acetic anhydride and left to stand at room temperature for 4 days.

To the resultant mixture, 100ml of benzene was added and the resulting mixture was washed three times with water. The benzene layer was gathered and evaporated to dryness.

The water layer was added with sodium bicarbonate to adjust the pH value to 8 and then extracted again with benzene. This extract was also evaporated to dryness.

The first benzene was dissolved in a small amount of benzene, charged into a column (2.7 × 16cm) filled with silica gel, and developed with benzene-acetone(9:1). The effluent was collected into 8-gram fractions. The fractions of numbers 11–14 were gathered together and evaporated to dryness to obtain 662mg of the 9,2'-diacetyl-3''-thiomethoxymethyl-SF-837 substance. The second benzene extract, when being treated in the same manner, gave a further 60mg yield of this substance. The physical and chemical properties of this substance was:

Melting point: 100°–104° C (Amorphous) 120°–124° C (Crystalline, crystallized from cyclohexane)

Molecular weight as determined: 957 by mass spectrometry.

Absorption in NMR analysis: 4.6, 2.18 (thiomethoxymethyl group) (in heavy chloroform) 1.99 (acetyl group)

Elementary analysis: $C_{47}H_{75}NO_{17}S$, Calculated: C 58.91, H 7.89, N 1.46, S 3.35(%), Found: C 58.70, H 7.80, N 1.20, S 3.00(%).

Seven hundred and twenty five mg of the 9,2'-diacetyl-3''-thiomethoxymethyl-SF-837 substance was dissolved in 30ml of methanol and then admixed with 10% of water. After standing at room temperature for overnight, the mixture was poured into ice-water, the pH adjusted to 8 with sodium bicarbonate, and extracted with benzene. The benzene extract obtained was evaporated to dryness to obtain 547mg of the 9-acetyl-3''-thiomethoxymethyl-SF-837 substance whose properties were as follows:

Melting point: 119°–124° C (amorphous)

Molecular weight as determined: 915 by mass spectrometry

Elementary analysis: $C_{45}H_{73}NO_{16}S$

Calculated: C 59.00, H 8.03, N 1.53, S 3.50(%), Found: C 58.85, H 7.98, N 1.40, S 3.30(%).

EXAMPLE 2

Example 1 was repeated with 1 gram of 9,2'-dipropionyl-SF-837 substance, instead of 9,2'-diacetyl-SF-837 substance, as starting material to obtain 500mg of the 9,2'-dipropionyl-3''-thiomethoxymethyl-SF-837 substance of which property was as follows:

Melting point: 115°–120° C (amorphous) 132–136° C (crystalline, from cyclohexane)

Elementary analysis: $C_{49}H_{79}NO_{17}S$, Calculated: C 59.67, H 8.07, N 1.42, S 3.25(%), Found: C 59.50, H 8.00, N 1.26, S 3.10(%).

Five hundred mg of the 9,2'-dipropionyl-3''-thiomethoxymethyl-SF-837 substance was dissolved in 50ml of methanol. The resulting solution was admixed with 10% of water and then left to stand at 40° C for one day. Afterwards, the reaction mixture was treated in the same manner as in Example 1 to obtain 400mg of the 9-propionyl-3''-thiomethoxymethyl-SF-837 substance whose properties were as follows:

Melting point: 115°–120° C (amorphous), 193°–194.5° (crystalline, from isopropanol).

Elementary analysis: $C_{46}H_{75}NO_{16}S$, Calculated: C 59.40, H 8.13, N 1.51 S 3.45(%). Found: C 59.40, H 8.00, N 1.48, S 3.11(%).

EXAMPLE 3

One gram of the 9-monoacetyl-SF-837 substance, instead of the 9,2'-diacetyl-SF-837 substance, was treated with dimethylsulfoxide and acetic anhydride to obtain 450mg of the 9,2'-diacetyl-3''-thiomethoxymethyl-SF-837 substance whose melting point was 100°–104° C (amorphous).

EXAMPLE 4

Ten grams of 9,2'-diacetyl-SF-837 substance was dissolved in a mixture of dimethylsulfoxide(200ml), acetic anhydride(50ml) and pyridine(10ml). The solution was kept at 28° C for 25 hours, and then poured into ice-water containing excess amount of sodium bicarbonate. The precipitate formed was extracted three times with benzene(200ml). And, the benzene extracts were combined, washed with water, dried over sodium sulfate and concentrated to dryness to yield the crude product(9.5g). This crude product was dissolved in hot cyclohexane(200ml) and the insoluble material was filtered off while it was hot. And upon cooling crystalline, 9,2'-diacetyl-3''-thiomethoxymethyl-SF-837 substance (7.3g) was obtained whose melting point was 120°–124° C.

What we claim is,

1. 9-acyl-3''-thiomethoxymethyl-SF-837 having the formula:

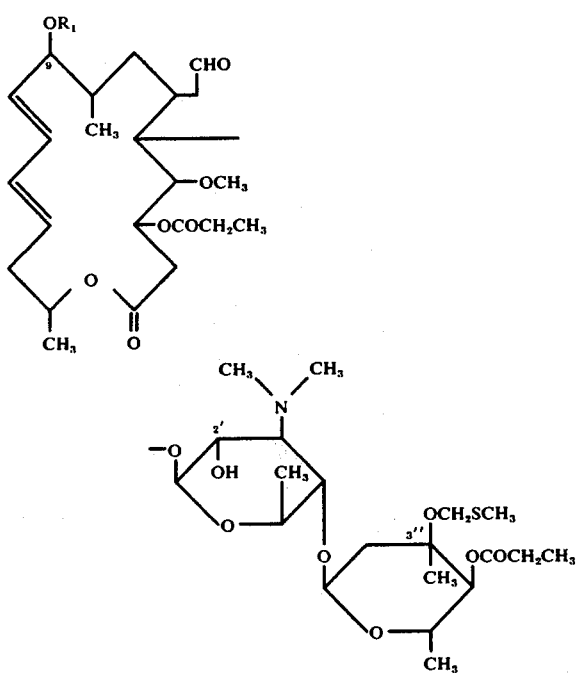

wherein $R_1$ represents acetyl or propionyl.

2. The compound according to claim 1 wherein $R_1$ is acetyl.

3. The compound according to claim 1, wherein $R_1$ is propionyl.

4. Process for manufacturing the compound, according to claim 1, which comprises in a first step, reacting a 9,2'-diacyl-SF-837 compound or 9-acyl-SF-837 compound having the formula:

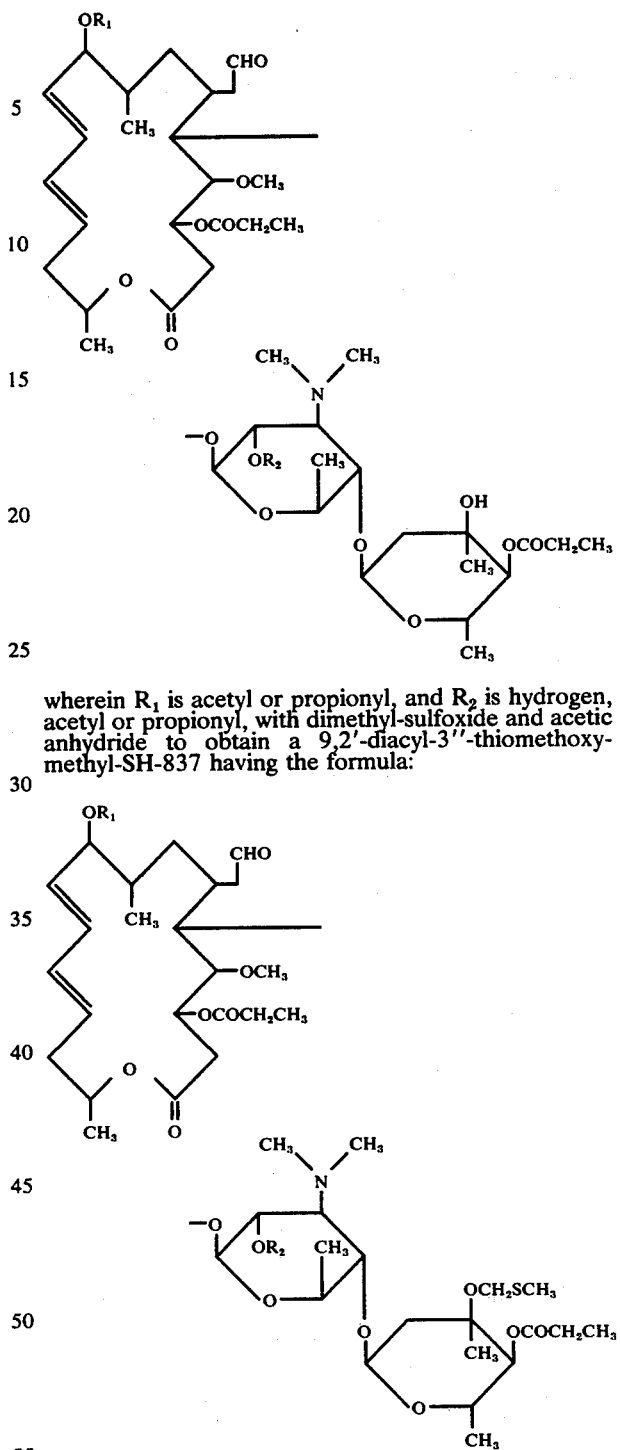

wherein $R_1$ is acetyl or propionyl, and $R_2$ is hydrogen, acetyl or propionyl, with dimethyl-sulfoxide and acetic anhydride to obtain a 9,2'-diacyl-3''-thiomethoxymethyl-SH-837 having the formula:

5. The process according to claim 4, wherein the second-step is carried out at about 40° C for about 12 – 24 hours and wherein $R_2$ is propionyl.

6. The process according to claim 4, wherein the first-step reaction is carried out at a temperature range of from room temperature to about 50° C.

7. The process according to claim 6, wherein the said reaction is carried out at room temperature for 1–5 days.

8. The process according to claim 6, wherein the said reaction is carried out in the presence of pyridine.

9. The process according to claim 4, wherein the second-step treatment is carried out at room temperature for overnight when the $R_2$ represents an acetyl group.

* * * * *